United States Patent [19]

Gordon et al.

[11] Patent Number: 4,599,049
[45] Date of Patent: Jul. 8, 1986

[54] HIGH PRESSURE METER PUMP

[75] Inventors: Gary Gordon, Saratoga; Kent Vincent, Cupertino, both of Calif.

[73] Assignee: Hewlett-Packard Company, Palo Alto, Calif.

[21] Appl. No.: 626,482

[22] Filed: Jul. 2, 1984

Related U.S. Application Data

[63] Continuation of Ser. No. 338,766, Jan. 11, 1982, abandoned.

[51] Int. Cl.⁴ .................. F04B 23/08; F04B 35/02
[52] U.S. Cl. ..................... 417/205; 417/248; 417/388; 417/517; 417/519; 417/540
[58] Field of Search ............. 417/205, 413, 385, 388, 417/248, 246, 540, 265, 419, 415, 519, 517, 518

[56] References Cited

U.S. PATENT DOCUMENTS

| | | | |
|---|---|---|---|
| 2,578,746 | 12/1951 | Scherger et al. | 417/388 |
| 2,606,430 | 8/1952 | Pownall | 417/246 |
| 2,627,813 | 2/1953 | Gilmore | 417/517 |
| 2,753,805 | 7/1956 | Boivinet | 417/388 |
| 3,838,948 | 10/1974 | McCorrey | 417/419 |
| 3,976,400 | 8/1976 | Major | 417/248 |
| 4,003,679 | 1/1977 | McManigill | 417/246 |
| 4,089,624 | 5/1978 | Nichols et al. | 417/419 |
| 4,245,963 | 1/1981 | Hutchins et al. | 417/540 |
| 4,321,014 | 3/1982 | Eburn, Jr. et al. | 417/27 |
| 4,326,837 | 4/1982 | Gilson et al. | 417/12 |

FOREIGN PATENT DOCUMENTS

| | | |
|---|---|---|
| 491336 | 5/1937 | United Kingdom . |
| 583390 | 8/1944 | United Kingdom . |
| 854565 | 1/1959 | United Kingdom . |
| 1530967 | 10/1977 | United Kingdom . |

*Primary Examiner*—Cornelius J. Husar
*Assistant Examiner*—Peter M. Cuomo
*Attorney, Agent, or Firm*—Jeffery B. Fromm

[57] ABSTRACT

A high pressure meter pump system with improved accuracy is provided by subdividing a large meter pump capacity into metered subvolume charges which are incrementally delivered to a high pressure slave pump.

This enables the pump sytem to achieve improved accuracy independent of flow rate and therefore increasing the range of flow rates available with acceptable accuracy. Additionally, the pump system self-primes independently of flow rate and therefore does not require degassing of the solvent being pumped.

31 Claims, 2 Drawing Figures

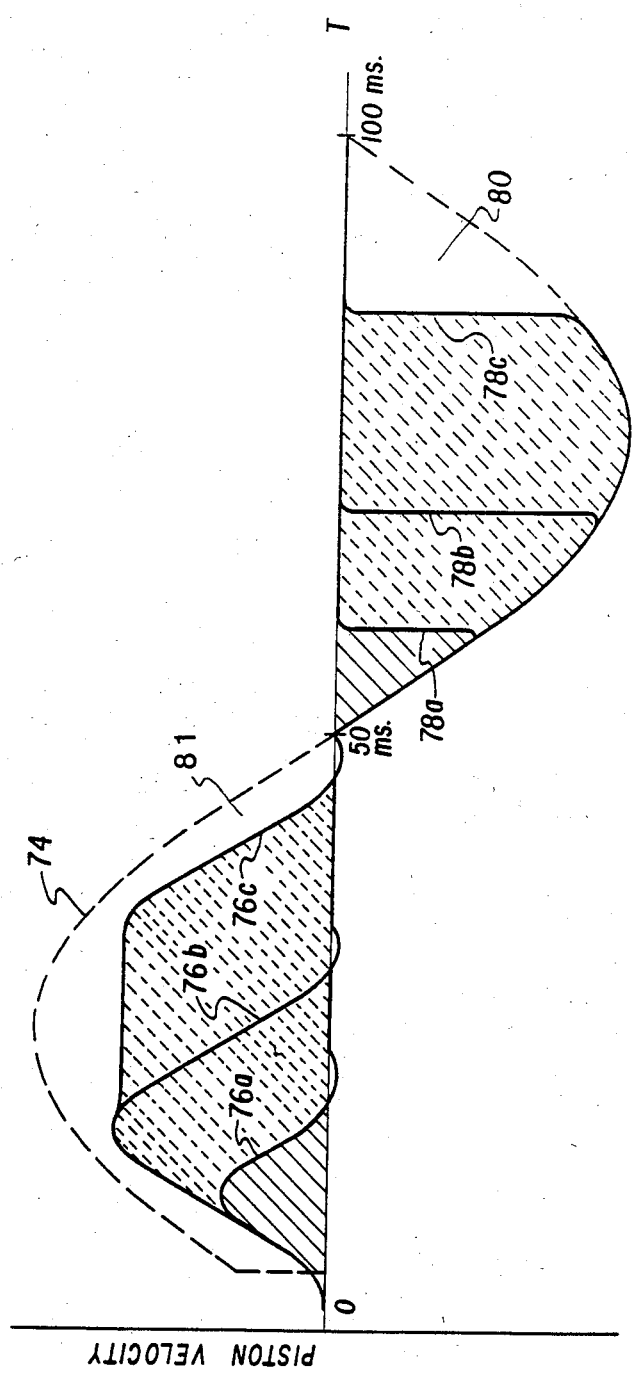

HIGH PRESSURE METER PUMP

CROSS REFERENCE TO RELATED APPLICATION

This is a continuation of application Ser. No. 338,766, filed Jan. 11, 1982, now abandoned.

BACKGROUND OF THE INVENTION

There is a need in liquid chromatography for solvent pump systems which can deliver fluids in accurately metered amounts. It is important in such systems that solvent flow be precisely controlled independently of the load pressure. Liquid chromatography systems and particularly systems utilizing gradient elution require high accuracy at extremely low flow rates. For example, in micro-bore chromatography it is desirable to resolve flow rates as low as one microliter per minute. It has been a problem with most prior art devices that the compressibility of the fluid and the mechanical compliance of the pump combine to cause a severe drop in flow rate as load pressure increases, this phenomenon being commonly referred to as "roll off". A two pump system overcomes inaccuracies due to roll off by utilizing a low pressure meter pump which injects controlled amounts of solvent into a high pressure slave pump. The meter pump is synchronized with the slave pump to insure that the meter pump delivers its metered charge into a low pressure portion of the slave pump cycle. Because the meter pump always operates into a low pressure load, roll off is not a problem affecting meter pump accuracy. Such a pump system is disclosed in U.S. Pat. No. 4,003,679 HIGH PRESSURE PUMP WITH METERING by Douglas McManigill and assigned to the assignee of the present application.

The McManigill specification describes a system in which the meter pump/slave pump pair are mechanically coupled to cycle at the same fixed rate. Flow rate is controlled by mechanically adjusting meter pump displacement. However, mechanical and fluid compliance in the meter pump introduces some error in each meter pump cycle. This error tends to increase as a function of increasing meter pump cycle rate. As flow rate and hence meter pump displacement is reduced this error and others inherent in scaling become an increasingly greater percentage of the volume of fluid pumped. Any such error is reproduced in each cycle of the meter pump/slave pump pair and reduces system flow rate accuracy, particularly at low flow rates. Hence, the range of flow rates over which a given meter pump can operate is limited by degradation of accuracy. Difficulty in self-priming may also become a problem at low flow rates in pumps that adjust flow rate by controlling displacement because larger displacement pumps tend to self-prime better than small displacement pumps.

SUMMARY OF THE INVENTION

The present invention overcomes problems with inaccuracy associated with roll off by utilizing a meter pump/slave pump pair as in the McManigill patent. However, further improvements in accuracy are attained by using a servo-driven syringe-type meter pump delivering a charge into a diaphragm slave pump. The volume of the meter pump syringe cylinder is designed to be many times greater than the capacity of the slave pump, so that the slave pump cycles many times for each meter pump cycle. Error in the syringe-type meter pump is very low when expressed as a percentage of the volume of solvent pumped in each meter pump cycle. Because the meter pump is driven by a servomotor at a much lower cycle rate than the slave pump, the small meter pump error is distributed over many slave pump cycles. Consequently, flow rate accuracy is independent of the volume of fluid being pumped. Thus the proposed system is able to resolve very low flow rates such as one microliter per minute. The servomotor may be synchronized to drive the meter pump only during the low pressure input portion of the slave pump cycle. Alternately, a compliance may be inserted between the meter pump and the slave pump allowing the meter pump to operate independently from the slave pump. Because of the nature of this meter pump/slave pump pair the system maintains high accuracy over a relatively broad range of flow rates. Additionally, the ability to self-prime is improved.

DESCRIPTION OF THE DRAWING

FIG. 2 shows several filling profiles for the system of FIG. 1.

DESCRIPTION OF THE PREFERRED EMBODIMENT

Figure 1:
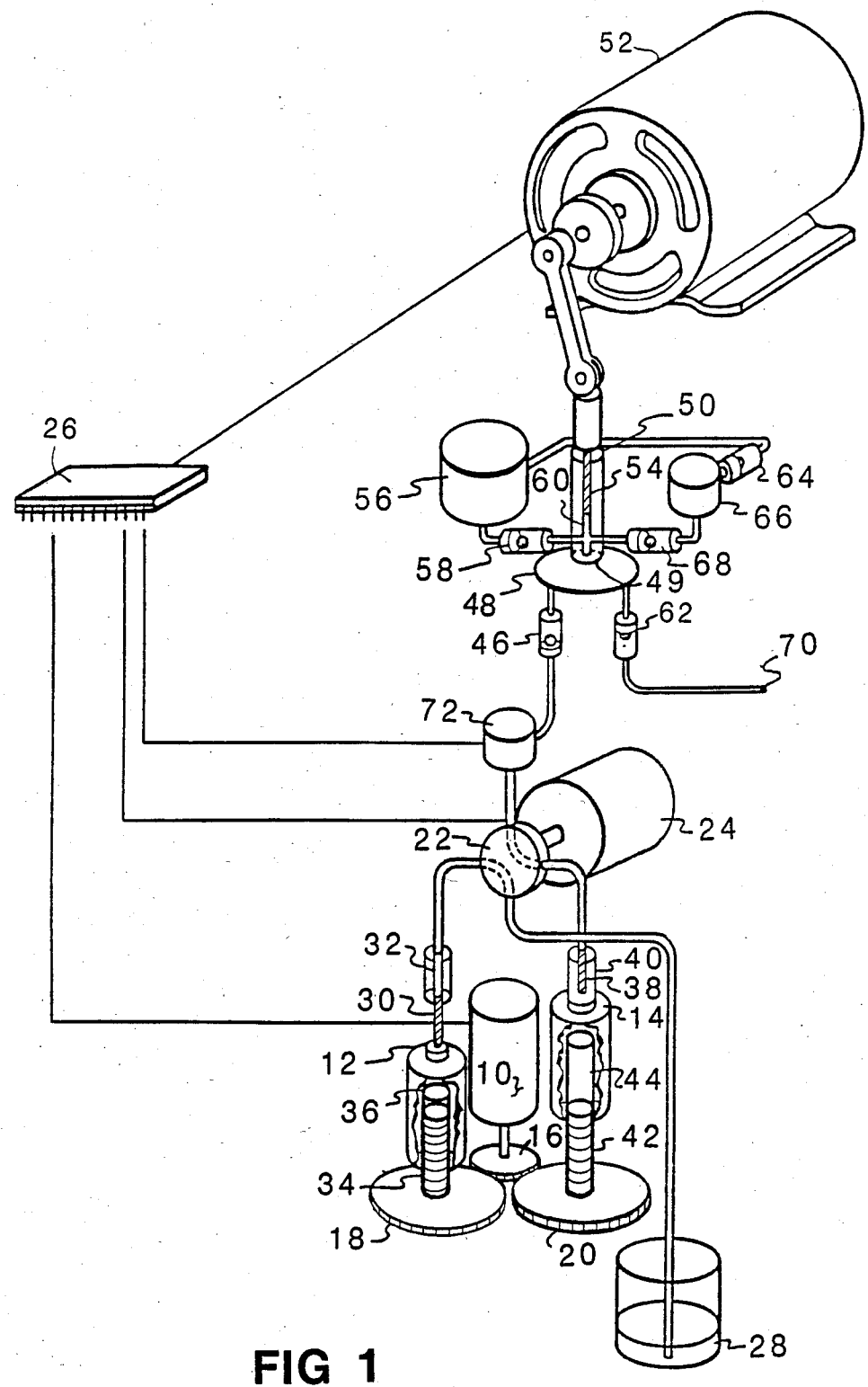
FIG. 1 illustrates a pumping system according to a preferred embodiment of the invention.

In FIG. 1, a servomotor 10 drives a pair of syringe-type meter pumps 12 and 14 connected in a push-pull mode. A piston 30 of meter pump 12 is raised and lowered relative to a piston cylinder 32 by engagement of a lead screw 34 with an interior threaded portion of a piston carrier 36. Similarly, a piston 38 in pump 14 is raised and lowered in a piston cylinder 40 by the engagement of a lead screw 42 with an interior threaded portion of a piston carrier 44. Pumps 12 and 14 always move equally in opposite directions in a push-pull mode because a gear 18 attached to threaded shaft 34 of pump 12 drives gear 20 attached to threaded shaft 42 of pump 14, and because gears 18 and 20 and thread pairs 34-36 and 42-44 are matched. Hence, the action of servomotor 10 connected to a gear 16 drives gears 18 and 20 equally in opposite directions. This in turn moves pistons 30 and 38 equal distances in opposite directions.

The flow pattern of the push-pull pair of meter pumps 12 and 14 is reversed by a 90 degree rotation of a four-way rotary valve 22 actuated by servomotor 24, which actuation is synchronized with a reversal of direction of servomotor 10. This sequence of changes may be controlled by a microprocessor 26, such as an Intel 8085 microprocessor, to insure that one of the meter pumps 12 or 14 is pumping while the other is refilling from a reservoir of solvent 28.

At any instant the meter pump which is then pumping, e.g., pump 14 as shown in FIG. 1, delivers its metered charge through a ball valve 46 into a diaphragm pump chamber 48 of a high pressure slave pump 50. A pump motor 52 raises a piston 54, drawing oil from a reservoir 56 through a check valve 58 into a piston cylinder 60. Diaphragm pump chamber 48 is seperated from piston cylinder 60 by a flexible diaphragm 49 such that solvent from meter pump 12 or 14 is not able to mix with oil from slave pump 50. The flexible diaphragm 49 transmits pressure between the oil in piston cylinder 60 and any solvent in diaphragm pump chamber 48. As piston 54 is driven down by motor 52, check valve 58 closes. A check valve 62 opens when the pressure in piston cylinder 60 exceeds load pressure. A spring-loaded ball valve 64, used as a back pressure regulator, together with a compliance 66 and a check valve 68 functions as a high pressure hydraulic override; it is adjusted to open at a pressure above the maximum load pressure. As piston 54 continues its downward movement, oil pressure builds up in piston cylinder 60. The pressure is transmitted across the flexible diaphragm 49 into the solvent in diaphragm pump chamber 48. If ball valve 46 is not already closed, it closes under the increased pressure in diaphragm pump chamber 48. As pressure in diaphragm pump chamber 48 reaches load pressure, check valve 62 opens discharging the solvent at load pressure through tube 70. After all solvent has been forced out of diaphragm pump chamber 48, oil pressure in piston cylinder 60 again rises, opening check valve 68 for the remainder of the downward stroke of piston 54. In this way slave pump 50 delivers the same volume of fluid (both solvent and oil) in every cycle. Excess capacity of slave pump 50 over the amount of solvent delivered by meter pump 12 or 14 to diaphragm pump chamber 48 is expended by pumping oil through check valve 64 into compliance 66 which is held at a pressure above maximum load pressure by adjustment of spring loaded ball valve 64. When the pressure in piston cylinder 60 decreases check valve 68 is closed by the pressure retained in compliance 66. Ball valve 64, however, will remain open as long as its adjusted opening pressure is below the pressure in compliance 66. In this way the high pressure hydraulic override is able to gradually release any retained excess pressure.

The pressure at which ball valve 46 is adjusted to open is such that it will not open solely as a result of the suction pressure caused by the upward motion of piston 54. This is to insure that only solvent actively delivered by meter pump 12 or 14 enters diaphragm pump chamber 48.

In operation, motor 52 drives slave pump 50 at a continuous rate while servomotor 10 incrementally subdivides the volume of meter pump piston cylinder 32 or 40 into subvolumes, delivering one such subvolume for each slave pump cycle. In this way the meter pump cycles much more slowly than the slave pump. Flow rate is controlled by regulating the size of the subvolumes. In a meter pump/slave pump pair as in preferred embodiment, for example, assume motor 52 is of the constant speed type and drives slave pump 50 through six hundred complete pump cycles per minute, and meter pump piston cylinders 32 and 40 have combined volumes of one-fifth of a milliliter, and require eight rotations (four clockwise plus four counterclockwise) (2,880 degrees) of threads 34 and 42 to deliver a volume of one-fifth of a milliliter. Then, at a first flow rate of twelve milliliters per minute, meter pump pair 12 and 14 must deliver one-fifth of a milliliter per second. To accomplish this, servomotor 10 must rotate gears 18 and 20 through six hundred equal incremental rotations of 288 degrees each, per minute. In contrast, a second flow rate of one microliter per minute (or one meter pump cycle in every 200 minutes) requires six hundred incremental rotations of 0.024 degrees each, per minute. In effect the twelve milliliter flow rate subdivides the combined one-fifth milliliter volume of meter pump piston cylinders 32 and 40 into ten subvolumes averaging 20 microliters each. At the one microliter flow rate each one-fifth milliliter volume is subdivided into 120,000 subvolumes averaging 0.001667 microliters each. Any error in the volume of a particular subvolume is compensated for through the integration of many subvolumes over time.

Microprocessor 26 can be programmed to synchronize servomotor 10 with synchronous motor 52 such that meter pump 12 or 14 only delivers solvent through ball valve 46 during the portion of the cycle of slave pump 50 when piston 54 is moving upwards. This insures that meter pump 12 or 14 always experiences minimal roll off. Alternatively, a compliance 72 would allow servomotor 10 to operate independently of synchronous motor 52 by storing solvent during the high pressure portion of the slave pump cycle. Another method of coordinating the action of slave pump 50 with the amount of solvent delivered by meter pump 12 or 14 is to combine a "smart" compliance 72 with a variable speed or variable displacement slave pump 50. In this way slave pump 50 would change the volume of fluid pumped in each cycle in response to the solvent delivered by meter pump 12 or 14 as communicated by "smart" compliance 72 to microprocessor 26. Finally, in liquid chromotography systems utilizing gradient elution the output from multiple meter pump pairs could be mixed and delivered to a single slave pump.

FIG. 2 shows a curve 74 representing the harmonic motion of the piston 54 during one cycle of operation of slave pump 52. Three curves 76a, 76b and 76c illustrate different possible filling profiles for filling of slave pump 52 by meter pumps 12 and 14. Curves 78a, 78b and 78c illustrate the corresponding delivery profiles for slave pump 50 for each of the filling profiles 76a, 76b and 76c. As discussed above, any excess capacity of slave pump 50 over the amount of solvent delivered to the slave pump is expended by pumping of oil by slave pump 50; in FIG. 2, this volume is indicated by refill area 81 and delivery area 80 both corresponding to solvent profiles 76c, 78c.

We claim:

1. A pumping system comprising:
   first pumping means for metering fluid charges of a preselected volume, for incrementally subdividing said preselected volume into metered charges having a desired subvolume and for delivering said metered subvolume charges against a predetermined first pressure; and
   second pumping means mechanically driven independently of said first pumping means and hydraulically interconnected with said first pumping means for receiving said metered subvolume charges and for delivering said metered subvolume charges to a load tube at a second pressure higher than said first pressure;
   said second pumping means including pressure establishing means for providing said predetermined first pressure against which said first pumping means delivers said metered charges and insuring that no charge is drawn into said second pumping means from said first pumping means by action of said second pumping means.

2. A pumping system as in claim 1 wherein:
   said first pumping means further comprises adjustment means for regulating a flow rate delivered by the first pumping means by changing the number of subvolume charges delivered per minute against the predetermined first pressure.

3. A pumping system as in claim 1 wherein said second pumping means further comprises a pumping cavity including a diaphragm dividing said pumping cavity from a pumping chamber; and said pressure establishing means further comprises:

intake means for receiving said metered subvolume charges in said pumping chamber at said first pressure;

exit means for discharging said metered subvolume charges from said pumping chamber to said load tube at said second pressure;

a reservoir containing reservoir fluid for supply to said pumping cavity; and piston means for drawing said reservoir fluid into said pumping cavity at a pressure below said first pressure and for expelling said reservoir fluid from said pumping cavity at a pressure greater than said second pressure for return to said reservoir.

4. A pumping system as in claim 1 wherein said first pumping means further comprises a plurality of independent pumps for metering, subdividing and delivering an associated plurality of fluids to said second pumping means.

5. A pumping system as in claim 1 wherein the second pumping means further comprises a first cyclic pump having a second volume equal to said subvolume, so that the first cyclic pump cycles one time to deliver each subvolume.

6. A pumping system as in claim 5 wherein the changes of pressure of the first pumping means and the first cyclic pump are synchronized to deliver the subvolume from the first pumping means to the first cyclic pump only during the low pressure input portion of the first cyclic pump cycle.

7. A pumping system as in claim 5 wherein the first pumping means further comprises a second cyclic pump, and the first and second cyclic pumps are synchronized to deliver the subvolume from the second cyclic pump to the first cyclic pump only during the low pressure input portion of the first cyclic pump cycle.

8. A pumping system as in claim 5 further comprising a compliance hydraulically connected between the first pumping means and the first cyclic pump, so that the first cyclic pump cycle need not be synchronized with the time at which the subvolume is delivered by the first pumping means.

9. A pumping system as in claim 2 wherein said second pumping means further comprises a pumping cavity including a diaphragm dividing said pumping cavity from a pumping chamber; and said pressure establishing means further comprises:

intake means for receiving said metered subvolume charges in said pumping chamber at said first pressure;

exit means for discharging said metered subvolume charges from said pumping chamber to said load tube at said second pressure;

a second reservoir containing a second fluid for supplying to said pumping cavity; and piston means for drawing said second fluid into said pumping cavity at a pressure below said first pressure and for expelling said second fluid from said pumping cavity at a pressure greater than said second pressure for return to said second reservoir.

10. A pumping system as in claim 2 wherein said first pumping means further comprises a plurality of independent pumps for metering, subdividing and delivering an associated plurality of first fluids to said second pumping means.

11. A pumping system as in claim 2 wherein the second pumping means further comprises a first cyclic pump having a second volume equal to said subvolume, so that the first cyclic pump cycles one time to deliver each subvolume.

12. A pumping system as in claim 11 wherein the changes of pressure of the pumping means and the first cyclic pump are synchronized to deliver the subvolume from the first pumping means to the first cyclic pump only during the low pressure input portion of the first cyclic pump cycle.

13. A pumping system as in claim 11 wherein the first pumping means further comprises a second cyclic pump, and the first and second cyclic pumps are synchronized to deliver the subvolume from the second cyclic pump to the first cyclic pump only during the low pressure input portion of the first cyclic pump cycle.

14. A pumping system as in claim 11 further comprising a compliance hydraulically connected between the first pumping means and the first cyclic pump, so that the first cyclic pump cycle need not be synchronized with the time at which the subvolume is delivered by the first pumping means.

15. A pumping system comprising:

first pumping means for metering fluid charges of a preselected volume of a first fluid, for incrementally subdividing said preselected volume into metered charges having a desired subvolume and for delivering said metered subvolume charges to a first load at a predetermined first pressure, said first pumping means having a first pumping piston having a first fluid port, a second pumping piston having a second fluid port, mechanical driving means coupled to the first and second pumping pistons for moving said first and second pumping pistons each through a push stroke and a pull stroke in push-pull fashion relative to each other and for incrementally subdividing each push stroke to provide the desired subvolume charges, a first reservoir for holding the first fluid, and fluid switch means interposed between the first fluid port and the first reservoir and between the second fluid port and the first reservoir for connecting the first pumping piston to the first reservoir while the first pumping piston is on the pull stroke and connecting the second pumping piston to the first load while the second pumping piston is on the push stroke when the fluid switch means is in a first position, and connecting the first pumping piston to the first load while the first pumping piston is on the push stroke and connecting the second pumping piston to the first reservoir while the second pumping piston is on the pull stroke when the fluid switch means is in a second position; and second pumping means mechanically driven independently of said first pumping means and hydraulically interconnected with said first pumping means for receiving said metered subvolume charges from said first load and for delivering said metered subvolume charges to a load tube at a second pressure higher than said first pressure, said second pumping means having pressure establishing means for providing said predetermined first pressure in said first load and insuring that no charge is drawn into said second pumping means from said first load by action of said second pumping means.

16. A pumping system as in claim 15 wherein:
said first pumping means further comprises adjustment means for regulating a flow rate delivered by the first pumping means by changing the number of subvolume charges delivered per minute against the predetermined first pressure.

17. A pumping system as in claim 15 wherein said second pumping means further comprises a pumping cavity including a diaphragm dividing said pumping cavity from a pumping chamber; and said pressure establishing means further comprises:
intake means for receiving said metered subvolume charges in said pumping chamber at said first pressure;
exit means for discharging said metered subvolume charges from said pumping chamber to said load tube at said second pressure;
a second reservoir containing a second fluid for supplying to said pumping cavity; and
piston means for drawing said second fluid into said pumping cavity at a pressure below said first pressure and for expelling said second fluid from said pumping cavity at a pressure greater than said second pressure for return to said second reservoir.

18. A pumping system as in claim 15 wherein said first pumping means further comprises a plurality of independent pumps for metering, subdividing and delivering an associated plurality of first fluids to said second pumping means.

19. A pumping system as in claim 15 wherein the second pumping means further comprises a cyclic pump having a second volume equal to said volume, so that the cyclic pump cycles one time to deliver each subvolume.

20. A pumping system as in claim 19 wherein said first load is a compliance having sufficient volume to hold at least a portion of one of said subvolume charges, and wherein cycles of said cyclic pump are not synchronized with the time at which the subvolume charges are delivered by the first pump means to the compliance.

21. A pumping system as in claim 19 wherein the changes of pressure of the first pumping means and the cyclic pump are synchronized to deliver the subvolume charges from the first pumping means to the cyclic pump only during the low pressure input portion of the cyclic pump cycle.

22. A pumping system as in claim 16 wherein said first pumping means further comprises a plurality of independent pumps for metering, subdividing and delivering an associated plurality of first fluids to said second pumping means.

23. A pumping system as in claim 16 wherein said second pumping means further comprises a pumping cavity including a diaphragm dividing said pumping cavity from a pumping chamber; and said pressure establishing means further comprises:
intake means for receiving said metered subvolume charges in said pumping chamber at said first pressure;
exit means for discharging said metered subvolume charges from said pumping chamber to said load tube at said second pressure;
a second reservoir containing a second fluid for supplying to said pumping cavity; and
piston means for drawing said second fluid into said pumping cavity at a pressure below said first pressure and for expelling said second fluid from said pumping cavity at a pressure greater than said second pressure for return to said second reservoir.

24. A pumping system as in claim 16 wherein the second pumping means further comprises a cyclic pump having a second volume equal to said subvolume, so that the cyclic pump cycles one time to deliver each subvolume.

25. A pumping system as in claim 24 wherein said first load is a compliance having sufficient volume to hold at least a portion of one of said subvolume charges, and wherein cycles of said cyclic pump are not synchronized with the time at which the subvolume charges are delivered by the first pump means to the compliance.

26. A pumping system as in claim 24 wherein the changes of pressure of the first pumping means and the cyclic pump are synchronized to deliver the subvolume charges from the first pumping means to the cyclic pump only during the low pressure input portion of the cyclic pump cycle.

27. A pumping system as in claim 15 wherein said mechanical driving means further comprises:
a motor;
first and second screws coupled to said first and second pumping pistons respectively; and
gears interposed between the motor and the first and second screws.

28. A pumping system as in claim 27 wherein said motor is a first reversible servomotor.

29. A pumping system as in claim 28 wherein the first reversible servomotor is controlled by a microprocessor.

30. A pumping system as in claim 15 wherein the fluid switch means comprises:
a four-way rotary valve; and
a second reversible servomotor coupled to the four-way rotary valve.

31. A pumping system as in claim 30 wherein the second reversible servomotor is controlled by a microprocessor.

* * * * *